(12) United States Patent
Xu et al.

(10) Patent No.: US 8,012,927 B2
(45) Date of Patent: Sep. 6, 2011

(54) PLATELET PROMOTING PROTEIN AND THE USAGE THEREOF

(76) Inventors: Peilin Xu, Hong Kong (CN); Yichen Ge, Zhangjiagang (CN); Yan Yang, Baotou, MN (US)

(\*) Notice: Subject to any disclaimer, the term of this patent is extended or adjusted under 35 U.S.C. 154(b) by 155 days.

(21) Appl. No.: 12/406,674

(22) Filed: Mar. 18, 2009

(65) Prior Publication Data

US 2010/0279938 A1    Nov. 4, 2010

Related U.S. Application Data

(62) Division of application No. 11/729,727, filed on Mar. 29, 2007, now abandoned.

(51) Int. Cl.
*A61K 38/00* (2006.01)

(52) U.S. Cl. .................................................. 514/1.1

(58) Field of Classification Search .................. None
See application file for complete search history.

(56) References Cited

U.S. PATENT DOCUMENTS 5,986,049 A    11/1999   Forstrom et al.

FOREIGN PATENT DOCUMENTS

| WO | 9833911 A1 | 8/1998 |
| WO | 9913076 A1 | 3/1999 |
| WO | WO 99/45116 | * 10/1999 |

OTHER PUBLICATIONS

<http://www.medterms.com/script/main/art.asp?articlekey=19775> —Definition of Hematopoiesis from Medicine Net—obtained Jan. 20, 2011.*
Definition of Thrombopoietin from Google Health < https://health.google.com/health/ref/Thrombocytopenia >—obtained Jan. 20, 2011.*
Archimbaudt et al., "A randomized, double-blind placebo-controlled study with pegylated recombinant human megakaryocyte growth and development factor (PEG-rHuMGDF) as an adjunet to chemotherapy for adults with de novo acute myeloid leukemia", Blood, Dec. 1999, pp. 3694-3701, vol. 9, No. 11.
Schiffer et al., "A double-blind, placebo-controlled trial of pegylated recombinant human megakaryocyte growth and development factor as an adjunct to induction and consolidation therapy for patients with acute myeloid leukemia", Blood, Apr. 2000, pp. 2530-2535, vol. 95, No. 8.
Nash et al., "Safety and activity of recombinant human thrombopoietin (rhTPO) in patients (pt) with delayed platelet recovery (DPR)", blood, 1997, 90 Suppl. 1:262a.
"Nomenclature and Symbolism for Amino Acids and Peptides"; European Journal of Biochemistry, 1984, 138.9-37.
Gyuris et al., "Cdi1, a Human G1 and S Phase Protein Phosphatase That Associates with Cdk2", Cell, Nov. 1993, pp. 791-803, vol. 75.
Matsumoto et al., "Molecular cloning and characterization of the human NUDC gene", Hum. Genet., 1999, pp. 498-504, vol. 104.
Kaushansky et al., "Cloning and expression of murline thrombopoietin cDNA and stimulation of platelet production in vivo", Nature, Jun. 1994, pp. 565-568, vol. 369.
Alves-Rosa et al., "Treatment with liposome-encapsulated clodronate as a new strategic approach in the management of immune thrombocytopenic purpura in a mouse model", Blood, Oct. 2000, pp. 2834-2840, vol. 96, No. 8.
Genbank Database: gi 12052969, available at: http://www.ncbi.nlm.nih.gov/entrez/viewer.fgci?db=protein&val=12052969.
Zhang et al., "Expression, Purification and Characterization of a New Ligand cDNA of c-Mpl in *E. coli*", High Technology report, 2003, pp. 25-28.
Zhang et al., "Different Construction for Human c-Mpl Ligand Expressed Plasmid and Their Optimizing Strategy for Expressation in *Escherichia coli*", A China Academic Journal Electronic Publishing House, Sep. 2003, pp. 59-62, vol. 42, No. 5.
Bornhurst et al.; "Purification of Proteins Using Polyhistidine Affinity Tags"; Methods in Enzymology, 2000, vol. 326, pp. 245-254.

* cited by examiner

*Primary Examiner* — Suzanne M. Noakes
(74) *Attorney, Agent, or Firm* — The Webb Law Firm

(57) ABSTRACT

The present invention discloses a protein that has strong affinity to thrombopoietin receptor (C-MPL) and the nucleotide sequences of the protein. The protein is capable of increasing the numbers of platelets and enhancing the blood clotting in vivo and is named as platelet promoting protein (PPP). The protein and its nucleotide sequences can be used for the treatment of blood diseases including thrombocytopenia.

5 Claims, 5 Drawing Sheets

SEQUENCE LISTING

<160> NUMBER OF SEQ ID NOS: 6

<210> SEQ ID NO 1
<211> LENGTH: 993
<212> TYPE: DNA
<213> ORGANISM: Homo sapiens

<400> SEQUENCE: 1

```
atgggcggag agcaggagga ggagcggttc gacggcatgt tgctggccat ggctcagcag      60
cacgagggcg gcgtgcagga gcttgtgaac accttcttca gcttccttcg acgcaaaaca     120 gacttttca ttggaggaga agaagggatg gcagagaagc ttatcacaca gactttcagc     180
caccacaatc agctggcaca gaagacccgg cgggagaaga gagcccggca ggaggccgag     240
cggcgggaga aggcggagcg gcggccagac ctggccaagg aagccaagtc agagacctca     300 gggcccccaga tcaaggagct aactgatgaa gaggcagaga ggctgcagct agagattgac     360
cagaaaaagg atgcagagaa tcatgaggcc cagctcaaga acggcagcct tgactcccca     420
gggaagcagg atactgagga agatgaggag aagatgagaa aggacaaagg aaaactgaag     480
cccaacctag gcaacggggc agacctgccc aattaccgct ggacccagac cctgtcggag     540
ctggacctgg cggtcccttt ctgtgtgaac ttccggctga aagggaagga catggtggtg     600
gacatccagc ggcggcacct ccgggtgggg ctcaaggggc agccagcgat cattgatggg     660
gagctctaca tgaagtgaa ggtggaggag agctcgtggc tcattgagga cggcaaggtg     720
gtgactgtgc atctggagaa gatcaataag atggagtggt ggagccgctt ggtgtccagt     780
gaccctgaga tcaacaccaa gaagattaac cctgagaatt ccaagctgtc agacctggac     840
agtgagactc gcagcatggt ggaaaagatg atgtatgacc agcgacagaa gtccatgggg     900
ctgccaactt cagacgaaca gaagaaacag gagattctga agaagttcat ggatcaacat     960
ccggagatgg attttccaa ggctaaattc aac                                   993
```

<210> SEQ ID NO 2
<211> LENGTH: 331
<212> TYPE: PRT
<213> ORGANISM: Homo sapiens

<400> SEQUENCE: 2

```
Met Gly Gly Glu Gln Glu Glu Glu Arg Phe Asp Gly Met Leu Leu Ala
 1               5                  10                  15

Met Ala Gln Gln His Glu Gly Gly Val Gln Glu Leu Val Asn Thr Phe
            20                  25                  30

Phe Ser Phe Leu Arg Arg Lys Thr Asp Phe Phe Ile Gly Gly Glu Glu
        35                  40                  45

Gly Met Ala Glu Lys Leu Ile Thr Gln Thr Phe Ser His His Asn Gln
    50                  55                  60

Leu Ala Gln Lys Thr Arg Arg Glu Lys Arg Ala Arg Gln Glu Ala Glu
65                  70                  75                  80

Arg Arg Glu Lys Ala Glu Arg Ala Ala Arg Leu Ala Lys Glu Ala Lys
                85                  90                  95

Ser Glu Thr Ser Gly Pro Gln Ile Lys Glu Leu Thr Asp Glu Glu Ala
            100                 105                 110

Glu Arg Leu Gln Leu Glu Ile Asp Gln Lys Lys Asp Ala Glu Asn His
        115                 120                 125

Glu Ala Gln Leu Lys Asn Gly Ser Leu Asp Ser Pro Gly Lys Gln Asp
    130                 135                 140
```

-continued

Thr Glu Glu Asp Glu Glu Asp Lys Asp Lys Gly Lys Leu Lys
145                 150                 155                 160

Pro Asn Leu Gly Asn Gly Ala Asp Leu Pro Asn Tyr Arg Trp Thr Gln
            165                 170                 175

Thr Leu Ser Glu Leu Asp Leu Ala Val Pro Phe Cys Val Asn Phe Arg
            180                 185                 190

Leu Lys Gly Lys Asp Met Val Val Asp Ile Gln Arg Arg His Leu Arg
        195                 200                 205

Val Gly Leu Lys Gly Gln Pro Ala Ile Ile Asp Gly Glu Leu Tyr Asn
    210                 215                 220

Glu Val Lys Val Glu Glu Ser Ser Trp Leu Ile Glu Asp Gly Lys Val
225                 230                 235                 240

Val Thr Val His Leu Glu Lys Ile Asn Lys Met Glu Trp Trp Ser Arg
            245                 250                 255

Leu Val Ser Ser Asp Pro Glu Ile Asn Thr Lys Lys Ile Asn Pro Glu
            260                 265                 270

Asn Ser Lys Leu Ser Asp Leu Asp Ser Glu Thr Arg Ser Met Val Glu
        275                 280                 285

Lys Met Met Tyr Asp Gln Arg Gln Lys Ser Met Gly Leu Pro Thr Ser
    290                 295                 300

Asp Glu Gln Lys Lys Gln Glu Ile Leu Lys Lys Phe Met Asp Gln His
305                 310                 315                 320

Pro Glu Met Asp Phe Ser Lys Ala Lys Phe Asn
            325                 330

<210> SEQ ID NO 3
<211> LENGTH: 35
<212> TYPE: DNA
<213> ORGANISM: Artificial
<220> FEATURE:
<223> OTHER INFORMATION: Primer

<400> SEQUENCE: 3
ccggaattcc aagatgtctc cttgctggca tcaga                                    35

<210> SEQ ID NO 4
<211> LENGTH: 32
<212> TYPE: DNA
<213> ORGANISM: Artificial
<220> FEATURE:
<223> OTHER INFORMATION: primer

<400> SEQUENCE: 4
ccgctcgagt tatccgacca cgagctccag gg                                       32

<210> SEQ ID NO 5
<211> LENGTH: 32
<212> TYPE: DNA
<213> ORGANISM: Artificial
<220> FEATURE:
<223> OTHER INFORMATION: primer

<400> SEQUENCE: 5
cgggatccga tgggcggaga gcaggaggag ga                                       32

<210> SEQ ID NO 6
<211> LENGTH: 32
<212> TYPE: DNA
<213> ORGANISM: Artificial
<220> FEATURE:
<223> OTHER INFORMATION: primer

```
<400> SEQUENCE: 6 ccgctcgagctagttgaatttagccttggaaa                                    32
```

PLATELET PROMOTING PROTEIN AND THE USAGE THEREOF

CROSS REFERENCE TO RELATED APPLICATION

This application is a Divisional of U.S. patent application Ser. No. 11/729,727, filed Mar. 29, 2007, which is a Continuation-in-Part of PCT Application No. PCT/CN04/001358, filed Nov. 26, 2004.

FIELD OF THE INVENTION

The present invention relates to a bio-medicament, and more specifically relates to a protein for increasing the numbers of platelets and its applications in the treatment of blood diseases.

BACKGROUND OF THE INVENTION

As an important component of blood, platelets are responsible for hemostasis in response to vascular injury and involved in the repairment of injured blood vessels. Low level of blood platelets can be life-threatening as it is prone to a mass loss of blood. At the present, platelet transfusion is a top choice for treatment for patients of thrombocytopenia. However, like other blood products, the platelets are short in shelf life, and are easy to be contaminated with blood pathogens such as hepatitis B virus and AIDS virus, and often elicit allergenic reactions among recipients.

Thrombopoietin (TPO) plays its role of growth factor for thrombopoiesis by binding to its receptor MPL, which is made up of three parts, MPL-EC$_{(26-491aa)}$ (extracellular domain), transmembrane domain, and cytoplasmic domain. In 1994, five groups of scientists simultaneously cloned TPO. The successful cloning of TPO had injected new hopes and approaches for the treatment of thrombocytopenia. However, the clinical data indicated that the efficacy of TPO towards thrombocytopenia varied among patients. At the same time, the side effects of TPO were also observed. Two of the major side effects were: [1] TPO activated platelets, stimulated its aggregation, and thus lead to the formation of blood clotting; and [2] antibodies to TPO being generated after TPO administration (Archimbaud E, et al. Blood. 1999; 94:3694-3701; Schiffer CA, et al, Blood. 2000; 95:2530-2535; Nash R, et al. Blood. 1997; 90 suppl. 1:262a). The search for alternative therapeutic proteins or cytokines continues in the art.

The yeast two-hybrid system is a suitable system for the study of protein-protein interactions. The system, which contains two expression plasmids (plasmid A and plasmid B) as well as a yeast host, takes advantage of the fact that yeast transcription factors, such as LEXA or Ga14, comprises two separate domains: DNA-binding domain (DNA-BD) and transcription activating domain (AD). Plasmid A expresses a fusion protein of a bait protein and the DNA-BD; and Plasmid B expresses a fusion protein of a protein of interest and AD. After co-transformation of the two plasmids into the yeast host, the interaction of the bait protein and the protein of interest brings the DNA-BD and AD into close contact, which activates the transcription of the reporter gene. Therefore the system can be used to isolate ligands of bait proteins. The kits Matchmaker Two-Hybrid System 3, Matchmaker LexA Two-Hybrid System (Clontech) are commercially-available examples of the system.

SUMMARY OF THE INVENTION

The object of the current invention is to provide an isolated protein that has a function equivalent to the TPO.

The current invention also provides a nucleotide sequence for encoding the protein of the present invention and a plasmid that containing the DNA sequence.

Another object of the current invention is to provide the application of the protein, including using the protein as a medicament for treatment of a blood disease.

The current invention is carried out by using a yeast two-hybrid system, in particular, by using the extracellular domain of MPL (MPL-EC) as a bait protein to screen proteins in a human fetal liver cDNA library that interact with the MPL. The screening identified a protein that binds specifically to the extracellular domain of MPL. The protein of the present invention has 331 amino acids in length and has no homology to TPO in BLAST analysis. It is capable of stimulating the maturation of megakaryocytes and the formation of platelets and is consequently named as Platelet Promoting Protein, or PPP. The amino acid sequence of the PPP is shown as Sequence 2 in the Sequence Listing and its nucleic acid sequence is shown as Sequence 1 in Sequence Listing. The Platelet Promoting Protein or PPP of the present invention refers to the protein having the amino sequence as shown by Sequence 2 in the Sequence Listing.

Also provided by the invention are derivatives of the PPP. The derivatives of the "PPP" include: [1] mutants of the PPP, provided that the mutants retain the ability of increasing the numbers of platelets and enhancing the blood clotting in vivo; [2] variants of the PPP, which, as compared with the Sequence 2, comprise one or more conservative substitutions of amino acids; one or more deletions of amino acids; or one or more additions of amino acids; [3] a carboxyl terminal-truncated form or amino terminal-truncated form of the PPP having the Sequence 2; [4] a tandem repetition of partial or complete Sequence 2; and [5] a fusion protein of the PPP having the Sequence 2 and another protein or cytokine. One of such derivatives, for example, carries additional 2-6 histidines at the N-terminus of the Sequence 2.

The IUPAC nomenclature and symbolism for amino acid abbreviations was used in the present invention (*European Journal of Biochemistry*, 138:9-37, 1984).

To complete the invention, the inventors first amplified and isolated a 1.3 kb MPL-EC cDNA from the total human DNA using PCR primers MPLEC-F and MPLEC-R, which are complementary to the ends of the MPL-EC and contain appropriate restriction sites. The MPL-EC fragment was restricted and ligated into the polyclonal site of pLexA to generate a plamid, named as pLexA-MPL-EC. The pLexA-MPL-EC and human fetal liver cDNA library were then co-transformed into *Saccharomyces cerevisiae* EGY48 and a positive clone was identified on an auxotrophic media and then DNA sequencing was conducted. The sequencing analysis of the positive clone revealed the clone had an insert having a nucleotide sequence shown as Sequence 1 in Sequence Listing. Its deduced amino acid sequence is given as Sequence 2 in Sequence Listing.

Insertion of PPP gene into expression vector pET-28b formed a expression vector, named as pET-PPP, which was subsequently transformed into *E. coli* BL21(DE3). The transformants were induced to produce His-PPP containing six continuous histidine residues at the N-terminus of the protein. The His-tag served as an affinity tag for the purification of PPP by using a cobalt-based immobilized metal affinity chromatography ($Co^{2+}$IMAC) column.

The purified PPP was injected into normal mice and the amount of the circulating platelets was measured and the bleeding times were monitored. The results indicated that the His-PPP stimulated significantly the formation of platelets and increased the amount of platelets in the circulating blood.

The PPP of the invention is a potential medicament for the treatment of thrombocytopenia or/and hemorrhage. The protein of the present invention may be formulated into injections, powders, tablets, capsules, solutions, suspensions, or emulsions. The medicament may be administrated by oral administration or may be administrated via subcutaneous injection, intravenous injection or intramuscular injection.

The present invention also provides a pharmaceutical composition comprising the PPP of the invention. The pharmaceutical composition may be prepared by mixing the PPP or the derivatives of the PPP that have the function of increasing the numbers of platelets, with pharmaceutically acceptable excipients. The excipients may be a liquid such as water, salines, phosphate buffers or albumin solutions; or a solid such as antioxidant agents, starches or dextrins. The pharmaceutical compositions are preferably to contain other hematopoietic growth factors such as interleukins, erythropoietins, macrophage colony stimulating factor (MCSF).

The PPP of present invention may be readily prepared in to various solutions by applying any known methods in the pharmaceutical field, such as by using a sterile saline, phosphate buffer and albumin solution. The concentration of the solution may range from 1 to 100 µg PPP per milliliter of the solution.

The PPP of the present invention may be administrated to patients in a dosage with the dosage of TPO as a reference, e.g. in the range of 1 to 1000 µg per kilogram of body weight per day. The dosage will be determined by a medically qualified physician, based on a variety of factors of the patients, including age, weight, severity of sickness, the cause and history of the disease.

The vectors and host cells described in the invention were obtained commercially. For example, pET-28b and *E. coli* BL21(DE3) were from Novagen, the yeast two hybrid system Matchmaker LexA Two-Hybrid System and Talon Metal Affinity Resin were from Clontech.

The current invention is further described with the figures and Examples. The invention is not limited by the detailed description provided in the Examples. Various modifications can be made by those skilled in the field and these modifications should be construed to fall within the scope of the invention defined by the Claims.

EXAMPLES

The examples presented below are for illustration of the invention only and are not intended to be regarded as the limitations of the invention. In the following examples, conventional practice or manufacturers' suggestion/protocol was followed in the cases where the conditions were not specified.

Example 1

Isolation of PPP that interacts with the extracellular domain of MPL by using a yeast two-hybrid system 1.1 Construction of a Bait Protein Plasmid pLexA-MPL-Ec The primers MPLEC-F and MPLEC-R, with EcoRI and XhoI incorporated, were synthesized based on the sequence of MPL-EC as follows:

```
MPLEC-F:
5'-CCGGAATTCCAAGATGTCTCCTTGCTGGCATCAGA-3';

MPLEC-R:
5'-CCGCTCGAGTTATCCGACCACGAGCTCCAGGG-3'.
```

Figure 1:
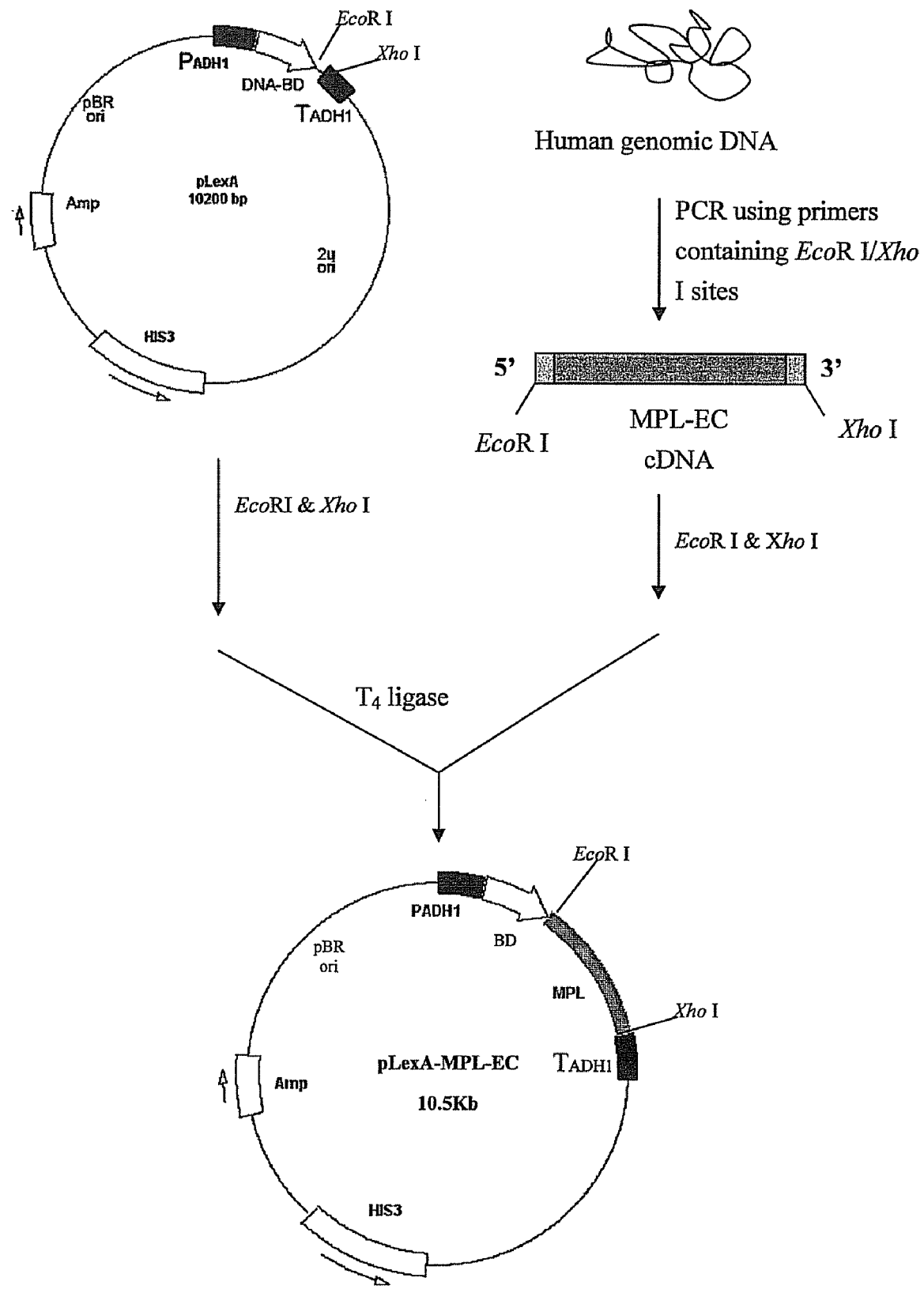
FIG. 1 shows the construction of plasmid pLexA-MPL-EC.
Figure 2:
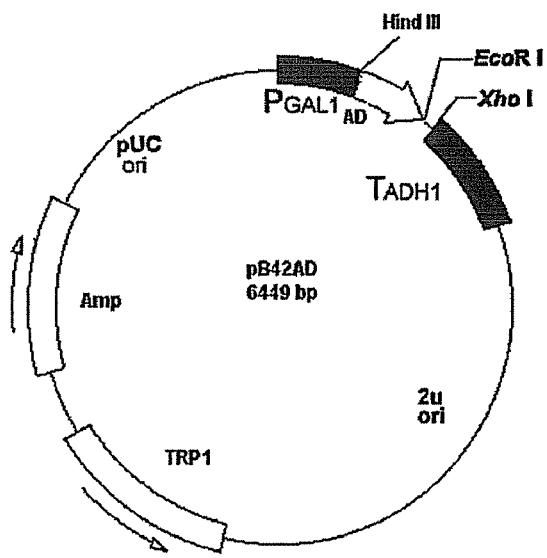
FIG. 2 shows the outline of plasmid pB42AD.

MPL-EC was PCR amplified with using the total human DNA as the template as indicated in FIG. 1. The PCR reaction mixture of a total 50 µl contained 1×PCR reaction buffer, 5 µM MPLEC-F, 0.5 µM MPLEC-R, 1 µg human total DNA, 2U Taq DNA polymerase (Fermentas), 50 µM dATP, 50 µM dTTP, 5.0 µM dCTP, 50 µM dGTP, 1.5 mM $MgCl_2$. The PCR program used was: 94° C., 5 min; then 30 cycles of 94° C., 1.5 min, 55° C., 1 min, 72° C., 2 min; with an additional of 72° C., 10 min at the end of the program. The resultant PCR product of approximately 1,450 bps long was separated by and purified from 1% agarose gel, digested using EcoRI and XhoI, and ligated by using T4 ligase into pLexA (Clontech) to generate pLexA-MPL-EC (FIG. 1).

1.2 Identification of PPP

The screening system MATCHMAKER LexA Two-hybrid System (Clontech) is based on LexA and used for the detection of protein-protein interaction in the yeast (Gyuris et al., 1993). The detailed procedure was carried out as described by the protocol of the manufacturer.

The human fetal liver cDNA library in pB42AD (Clontech) was diluted and spreaded on LB plates and incubated overnight at 37° C. The cell colonies were collected by using sterile cotton tips and transferred into a LB broth and incubated overnight at 37° C. The plasmids were isolated by using E.Z.N.A.® Fastfilter Plasmid Miniprep Kit (Omega Bio-Tek). One hundred µg of pLexA-MPL-EC DNA from Example 1.1 and 100 µg human fetal liver cDNA library DNA were co-transformed into *Saccharomyces cerevisiae* EGY48 containing p80p-lacZ ($Ura^+$, $Lac^+$, $Leu^+$); and the transformants were selected on SD/Gal/Raf/-His/-Trp/-Ura/-Leu auxotrophic medium containing X-Gal, prepared as suggested by the manufacturer. One positive clone of blue colony, named pB42AD-PPP, carrying an insert of approximate 1,300 bps was identified. The insert was sequenced and analyzed. The insert carried a complete coding region of 993 bps encoding a 331 amino acid peptide, as shown in Sequence 1 and Sequence 2. Blast analysis revealed that the sequence shares no homology with TPO but is identical to that of Human Nuclear Distribution Gene C (Matsumoto, N. and Ledbetter, D. H, Hum. Genet. 104, 498-504, 1999; Genbank database gi: 12052969). The protein was named as PPP, as it stimulates the formation of platelets (Example 3) and enhances the blood clotting function of platelets (Example 4).

Example 2

Figure 3:
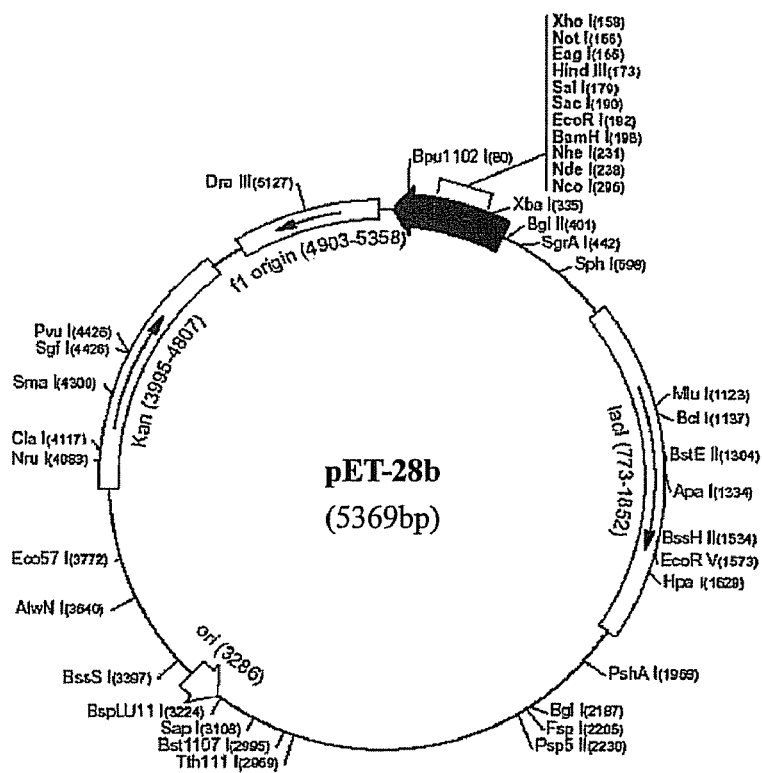
FIG. 3 shows the outline of expression vector pET-28b.

Construction of PPP Expression Vector pET-28b and the Expression and Purification of PPP PPP was cloned into His-tag containing expression vector pET-28B (Novagen) (FIG. 3). The expressed protein His-PPP carried six continuous histidine residues at the N-terminus and can be purified by affinity chromatography.

pET-28b contains multiple cloning sites. The primes PPP-F and PPP-R were designed based on the restriction sites on the vector and the cDNA sequence of PPP:

```
PPP-F: 5'-CGGGATCCGATGGGCGGAGAGCAGGAGGAGGA-3', containing BamHI (underlined);

PPP-R: 5'-CCGCTCGAGCTAGTTGAATTTAGCCTTGGAAA-3', containing XhoI (underlined).
```

Figure 4:
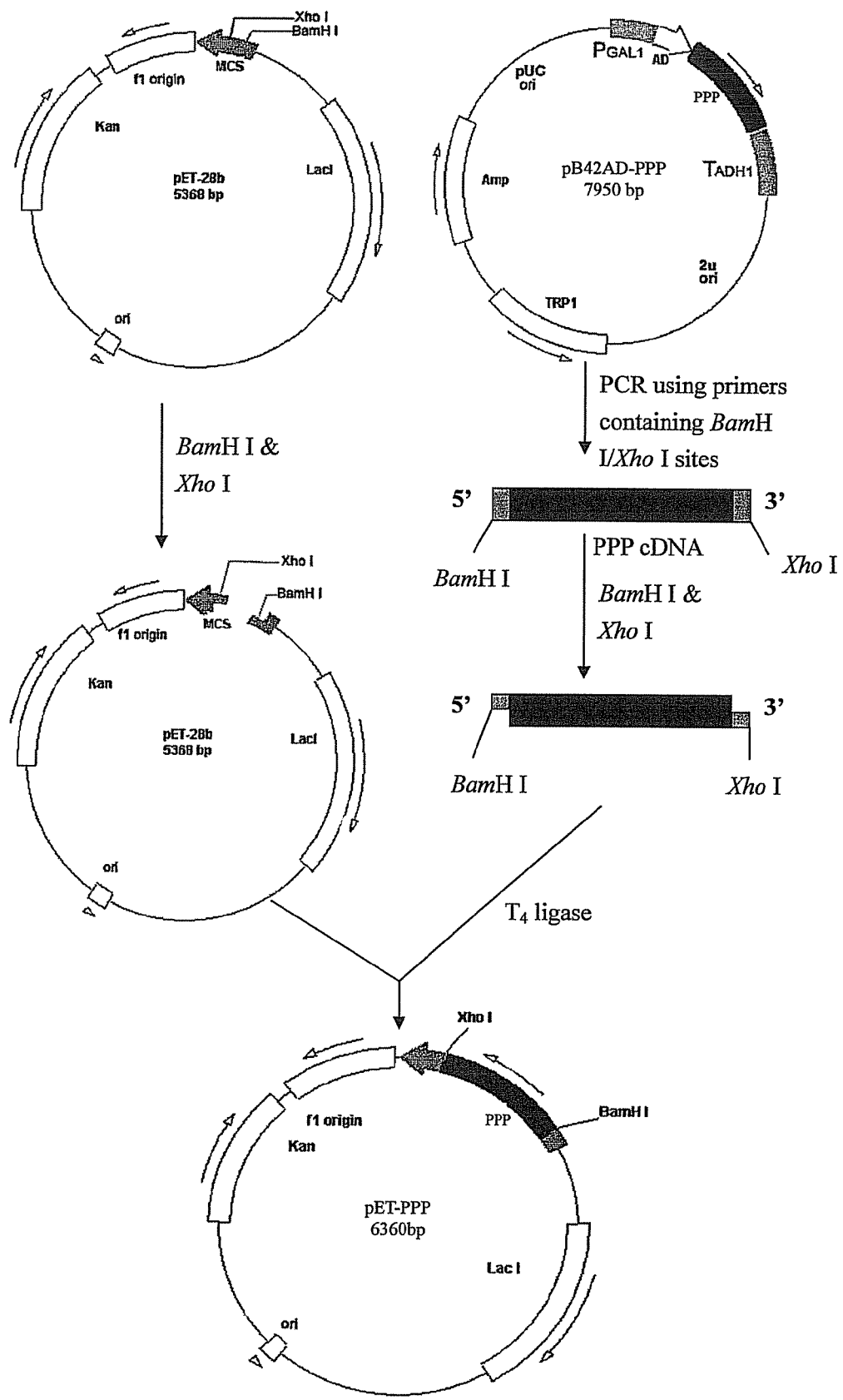
FIG. 4 shows the construction of the PPP expression vector pET-PPP.

PPP DNA was amplified with using pB42AD-PPP DNA as the template. The PCR reaction mixture of a total 50 μl contained 1×PCR reaction buffer, 0.5 μM PPP-F, 0.5 μM PPP-R, 1 μg pB42AD-PPP DNA, 2U Taq DNA polymerase (Fermentas), 50 μM dATP, 50 μM dTTP, 50 μM dCTP, 50 μM dGTP, 1.5 mM $MgCl_2$. The PCR program used was: 94° C., 5 min; then 30 cycles of 94° C., 1 min, 55° C., 1 min, 72° C., 1.5 min; and with an additional of 72° C., 10 min at the end of the program. The resultant PCR product of approximately 1,000 bps long was separated by and purified from 1% agarose gel, and digested by BamH1 and Xho1, and ligated into pET28b downstream and in frame with the His-tag to generate the construct pET-PPP (FIG. 4).

Figure 5:
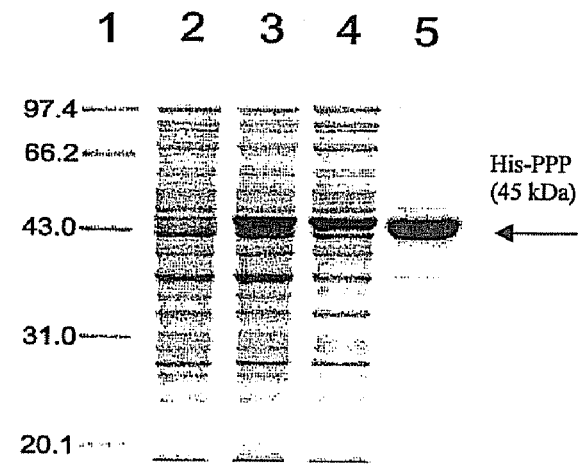
FIG. 5 shows SDS-PAGE of His-PPP. The protein samples were separated on 10% SDS-PAGE and stained with Coomassie blue. His-PPP, with a size of 45 kDa, was indicated by the arrow. Lane 1 shows a protein size ladder; lanes 2 and 3 shows *E. coli* cell lysates before and after IPTG induction, respectively; lane 4 shows a soluble His-PPP crude extract; and lane 5 shows the His-PPP after cobalt affinity chromatography ($Co^{2+}$IMAC) purification.

The pET-PPP was used to transform into *E. coli* strain BL21 (DE3), from Novagen. The transformant expressing His-PPP was grown in a LB medium containing 0.05 mg/ml kanamycin overnight at 37° C., and diluted 100 fold into the same medium and incubated at 37° C. to an $A_{600}$ of 0.5-0.6, and induced with 0.5 mM IPTG for 4 h at 30 C. The bacterial cells were collected by centrifugation, suspended with a phosphate buffer of pH 7.4 containing 50 mM sodium phosphate, pH 7.4, 300 mM NaCl, and 1 mM PMSF, lysed by sonication and centrifuged at 10,000 g for 30 minutes to remove cell debris. The His-PPP containing supernatants was purified by using cobalt-based immobilized metal affinity chromatography ($Co^{2+}$IMAC) column (Clontech) as described by the protocol of the manufacturer to yield a soluble His-PPP of 45 kDa in size. The protein was more than 95% pure on 10% SDS-PAGE (FIG. 5).

Example 3

His-PPP Stimulates Platelet Formation in BALB/C Mice

The procedures of protein injection and venous platelet measurement were based on Kaushansky et al., Nature, Vol. 369, 1994, 565-568 with modifications.

The His-PPP purified as described at Example 2 was diluted into a stock solution of 10 μg/ml with PBS containing 0.1% BSA and used for the injection. Thirty normal male BALB/c mice of 6-7 week old were divided randomly into three groups of ten mice each. The first group was subcutaneously injected with 10 μg/kg His-PPP once per day for seven consecutive days; the second group was subcutaneously injected with 50 μg/kg His-PPP once per day for seven consecutive day; and the third group (control) was subcutaneously injected with PBS containing 100 μg/ml of BSA once per day for seven consecutive days. Twenty μl venous blood was collected from a small lateral cut in the tail vein on day 0, 4, 7, 10, 13, 16 and 19. The platelets were counted using of an F-820 Sysmex electronic blood cell analyzer (Sysmex Corp Ltd., Japan).

Figure 6:
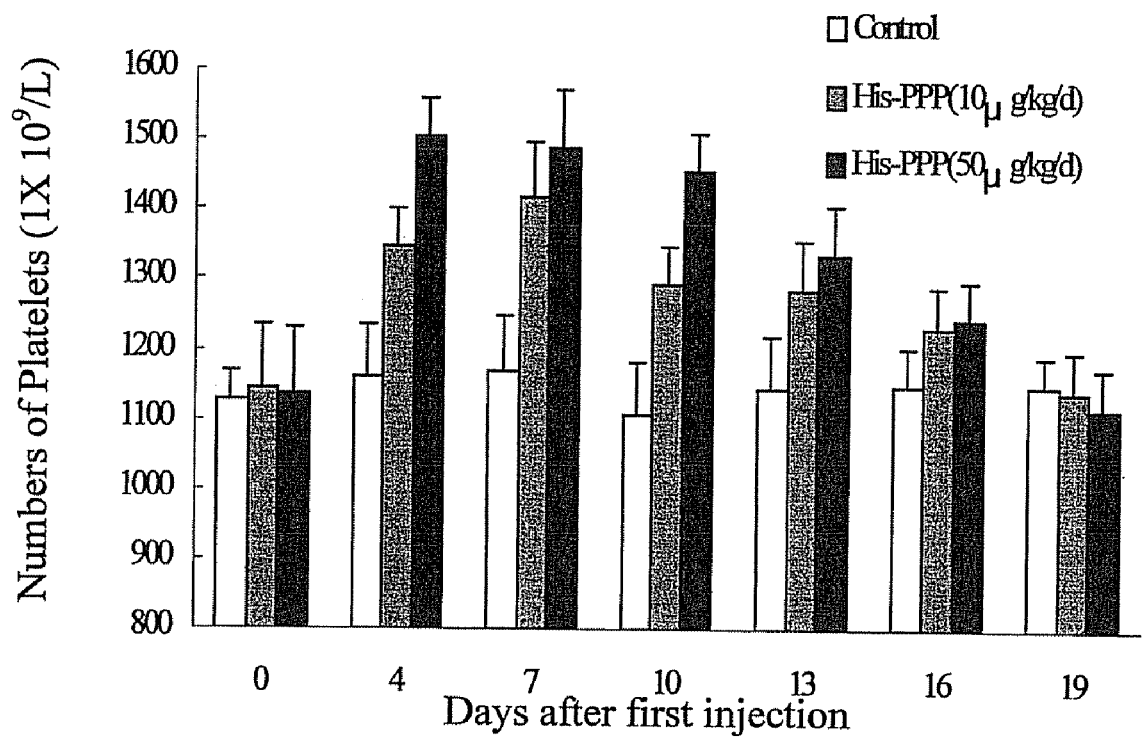
FIG. 6 shows the stimulation of platelet production by His-PPP in BALB/c mice. Normal BALB/c mice were subcutaneously injected with PBS (control, white column), or 10 µg/kg His-PPP (grey column), or 50 µg/kg His-PPP (black column) for 7 days. Twenty µL venous blood was collected from a small lateral cut in the tail vein on day 0, 4, 7, 10, 13, 16 and 19. The platelets were counted using an F-820 Sysmex electronic blood cell analyzer, and expressed as the mean±SD×$10^9$/L.

The results are shown in FIG. 6. At both dosages of His-PPP, significant increases (n=10, p<0.05) in platelet counts (expressed as mean±SD of platelets x $10^9$/L) were observed on day 4 and 7. On day 4, 10 μg/kg group generated 15.8% more platelets (1346±54; n=10, p<0.05) and 50 μg/kg group generated 29.6% more platelets (1506±70; n=10, p<0.01) than the control (1169±72, n=10). On day 7, 10 μg/kg group generated 21.3% more platelets (1418±80; n=10, p<0.05) and 50 μg/kg group generated 27.4% more platelets (1489±57; n=10, p<0.05) than the control (1108±71, n=10). The platelet numbers of the both treatment groups gradually declined after the completion of the injections and returned to preinjection levels on day 19, 12 days after the end of the injection.

Example 4

HIS-PPP Reduces the Bleeding Time in BALB/C Mice

The bleeding time test measures the time taken for the blood flow, caused by incision of the mouse tail veins, to stop. The hemostasis test evaluates the blood clotting function of the platelets. The measurement was conducted as described by Alves-Rosa et al., Blood, Vol. 96, 2000, 2834-2840 with modifications.

The His-PPP purified as described at Example 2 was diluted into a stock solution of 10 μg/ml with PBS containing 0.1% BSA and used for the injection. Twenty BALB/c mice were divided randomly into two groups of 10 mice each. The first group was subcutaneously injected with 10 μg/kg His-PPP once per day for seven consecutive days; the second group (control) was subcutaneously injected with PBS containing 100 μg/ml of BSA once per day for seven consecutive days. The bleeding times were recorded on day 0, 4, 7, 10, 13, 16 and 19. The measurement was as follows: a wound of 20 mm wide was made using scissors at the tails of the mice and the blood was removed by gently contacting the cut site with paper filters every 30 seconds until there was no blood stain on the filter. The duration between the initiation and stoppage of the bleeding was recorded as the bleeding time.

Figure 7:
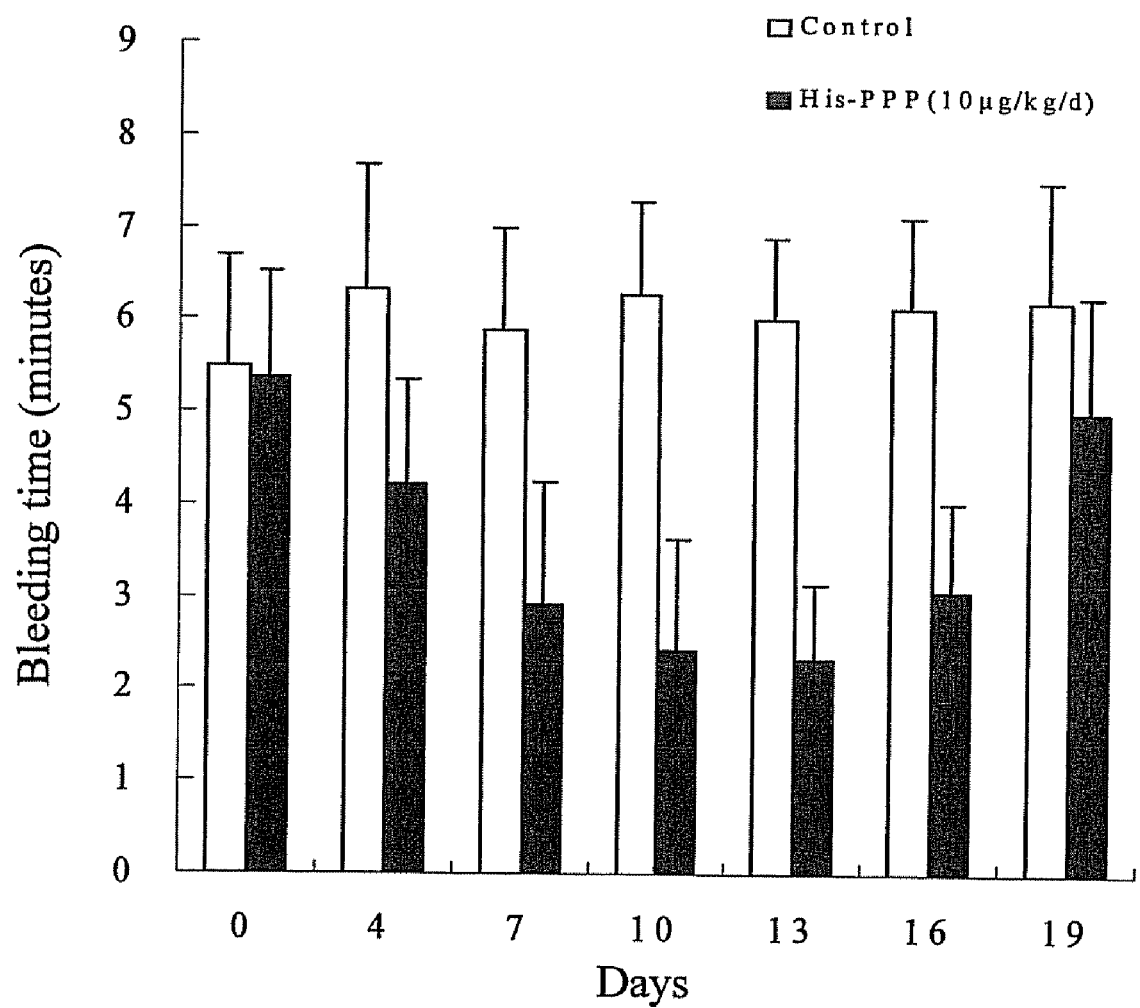
FIG. 7 shows the reduction of bleeding time by His-PPP in BALB/c mice. Normal BALB/c mice were subcutaneously injected with PBS (control, white column) or 10 µg/kg His-PPP (black column) for 7 days. The bleeding times were measured on day 0, 4, 7, 10, 13, 16 and 19.

The results are as FIG. 7 shows. On day 0, the bleeding times are almost identical for the two groups, both were around 5.5 minutes; on day 4, the bleeding time of His-PPP group was 4.2 minutes, 33.5% shorter than that of the control group (n=10, p<0.05)' on day 7, the bleeding time of His-PPP group was 2.9 minutes, 50.8% shorter than that of the control group (n=10, p<0.05); and on day 10, the bleeding time of His-PPP group was 2.4 minutes, 61.9% shorter than that of the control group (n=10, p<0.05). After the injection ended, the bleeding time of His-PPP group started to bounce back gradually and returned to the pre-injection level on day 19, i.e., 12 days after the last injection.

The invention is not limited by the detailed description provided in the Examples. Various modifications can be made by those skilled in the field and these modifications should be regarded as within the scope of the claims of the invention.

What is claimed is:

1. A method for treating a patient suffering from thrombocytopenia or hemorrhage, comprising the step of administrating to the patient an effective amount of a protein, wherein said protein is an isolated human-derived protein having the amino acid sequence set forth in SEQ ID NO:2; or a derivative thereof with a function of increasing the numbers of blood platelets.

2. The method according to claim 1, wherein the protein has additional 2-6 histidines at the N-terminus of the protein.

3. The method according to claim 1, wherein the amino acid sequence of the protein is encoded by the nucleotide sequence set forth in SEQ ID NO:1.

4. The method according to claim 1, wherein the protein is administrated in a form of injections, powders, tablets, capsules, solutions, suspensions, or emulsions.

5. The method according to claim 1, wherein the protein is in a form for oral administration or in a form for administration via subcutaneous injection, intravenous injection or intramuscular injection.

* * * * *